United States Patent
van Egmond (10) Patent No.: US 6,565,634 B1
(45) Date of Patent: May 20, 2003

(54) INJECTION LINER

(75) Inventor: Wil van Egmond, Cambridge (GB)

(73) Assignee: Atas International BV, Veldhover ( * ) Notice: Subject to any disclaimer, the term of this patent is extended or adjusted under 35 U.S.C. 154(b) by 0 days.

(21) Appl. No.: 09/914,370

(22) PCT Filed: Feb. 18, 2000

(86) PCT No.: PCT/GB00/00580
§ 371 (c)(1),
(2), (4) Date: Nov. 29, 2001

(87) PCT Pub. No.: WO00/50885
PCT Pub. Date: Aug. 31, 2000

(30) Foreign Application Priority Data

Feb. 25, 1999 (GB) ............................................... 9904225

(51) Int. Cl.⁷ ............................................... B01D 15/08

(52) U.S. Cl. ............................... 96/105; 96/106; 95/89

(58) Field of Search ................... 95/82–88; 96/101–107

(56) References Cited

U.S. PATENT DOCUMENTS

| | | | |
|---|---|---|---|
| 4,035,168 A | 7/1977 | Jennings | 55/67 |
| 4,066,183 A | 1/1978 | Armstrong | 215/247 |
| 4,162,977 A * | 7/1979 | Guillemin et al. | 96/105 X |
| 4,245,494 A | 1/1981 | Legendre et al. | 734/23.1 |
| 4,414,857 A | 11/1983 | Brazhnikov et al. | 73/863.11 |
| 4,422,860 A * | 12/1983 | Feinstein | 95/87 |
| 4,559,063 A * | 12/1985 | Munari et al. | 96/105 X |
| 5,006,315 A * | 4/1991 | Maroulis et al. | 96/104 X |
| 5,119,669 A | 6/1992 | Silvis et al. | 73/23.41 |
| 5,227,059 A * | 7/1993 | Shepherd | 96/105 X |
| 5,252,109 A | 10/1993 | Munari et al. | 95/87 |
| 5,347,844 A | 9/1994 | Grob et al. | 73/23.41 |
| 5,957,862 A * | 9/1999 | Wilson | 96/101 |
| 5,976,890 A * | 11/1999 | Gehre et al. | 96/105 X |
| 6,090,190 A * | 7/2000 | Enhsen et al. | 96/106 X |
| 6,090,278 A * | 7/2000 | Lally et al. | 96/106 X |

FOREIGN PATENT DOCUMENTS

| | | | | |
|---|---|---|---|---|
| DE | 1525794 | * | 7/1970 | 96/101 |
| DE | 2313301 | * | 9/1974 | 96/101 |
| DE | 2818719 | * | 12/1978 | 96/101 |
| DE | 3132638 | | 3/1983 | |
| GB | 1338199 | * | 11/1973 | 96/105 |
| GB | 1372356 | | 10/1974 | |
| JP | 63-122952 A | * | 5/1988 | 96/105 |
| JP | 63-124959 | | 5/1988 | |

OTHER PUBLICATIONS

Hinshaw, John V., "The Effects of Inlet Liner Configuration and Septum Purge Flow Rate on Discrimination in Splitless Injection", *Journal of High Resolution Chromatography*, vol. 16, Apr. 1993, pp. 247–253.

van Lieshout, Mark P.M., et al., "Programmed–temperature vaporiser injector as a new analytical tool for combined thermal desorption–pyrolysis of solid samples Application to geochemical analysis", *Journal of Chromatography A*, NL, Elsevier Science, vol. 764, No. 1, Mar. 1997, pp. 73–84.

(List continued on next page.)

Primary Examiner—Robert H. Spitzer
(74) Attorney, Agent, or Firm—Synnestvedt & Lechner LLP (57) ABSTRACT

A replaceable injection liner for a gas chromatograph is disclosed having a laterally extending external flange at its input end against which an injection septum is placed. A closure cap is positioned over and around the external flange and the injection septum to seal the septum against the flange, the septum closing and sealing the input end of the injection liner. The liner has a seal positioned beyond the flange to seal the interior surface of the injector and isolate it from the atmosphere and the injector's internal pressure.

21 Claims, 7 Drawing Sheets

OTHER PUBLICATIONS

European Patent Office Document, English language, Abstract of German Patent No. 3132638, issued Mar. 10, 1983, entitled "Method For Introducing Samples Into A Gas chromatograph, And Device For Carrying Out This Method".

Japanese Patent Abstract with figure, English language, Abstract of Japanese Patent No. 63–124959, issued May 28, 1988, entitled "Sample Injection Port Of Gas Chromatography".

* cited by examiner

INJECTION LINER

This invention is concerned with an injection liner, and relates in particular to a novel form of liner utilisable with a septum and cap and intended for use in the injector of a gas chromatograph.

Gas chromatography is a technique widely employed in industry. It finds particular application in the fields of medical care, pharmaceutical analysis, petroleum chemistry, petrochemicals and environmental analysis, and is especially valuable for the separation of complex mixtures into their components, typically such mixtures as contain organic chemicals, either as a simple mixture or in a solvent, such as water.

Basically, chromatography involves the transferring of a mixture of materials (the "sample mixture") by means of a flowing medium (the "mobile phase") along a passageway (the "column") containing a substance (the "stationary phase") to which the different components of the mixture are weakly, but differentially, attracted, so that gradually the less attracted components get ahead of the more attracted ones, and eventually, if the column is long enough, they are completely, separated. It is called "chromatography"—colour writing—after its original use, which was to separate mixtures of coloured dyes. In the case of gas chromatography, the mobile phase is a gas.

There are a number of different types of gas chromatography, but those in common use employ as the column a long tube containing the stationary phase. There are several designs of column, but typically it is long, narrow tube made from fused silica (like glass) coated on the outside with a polyimide or similar plastic layer to prevent corrosion and add strength. The silica tube may typically be from 5 to 50 meters (about 16 to 160 ft) long, and be of internal diameter 100 to 750 microns (0.0001–0.00075 m, or 0.01–0.075 cm, or about 0.004–0.03 in). The stationary phase chemical is either bonded on the inside of this tube or, in some cases, is deposited on solid, porous inert support materials which fill the tube.

When a small amount of the sample mixture is introduced to the inlet end of the column, with the mobile phase passing from the inlet end of the column to the outlet end, the mixture is blown slowly through the column. The stationary phase selectively slows down some of the compounds in the sample mixture, whereas other compounds are slowed much less or not at all. Compounds that are not slowed travel at the speed of the mobile phase, while compounds that are slowed down travel more slowly than the mobile phase. Because some compounds are slowed down and others are slowed less, those which are slowed less emerge from the far end of the column before those which are slowed more. Thus the mixture becomes separated into (some of) its components In operation, a very small amount of the sample mixture—typically one milligram or less—is injected into the inlet end of the column which is sealed into ant elongate tubular device called an injector. The injector facilitates the introduction of this small amount of sample into the system, provides the required carrier gas flow for the column, and may also perform other functions, including the evaporation and concentration of the sample. Gas from the injector flows through the column from the inlet, injector end, and the individual components of the mixture emerge separately from the outlet end of the column at a time that depends on the velocity of the carrier gas and the extent to which the components are slowed by the stationary phase.

These separated compounds are then passed into a device called a detector, which can simultaneously detect the presence of the components and, in general, measure the amount of each one present. The detector produces an electrical signal that is amplified and passed to data-processing equipment which measures both the time after injection that the component emerged from the column and also the amount of signal produced; it can then produce a report on the composition of the original mixture, which can be utilised by the User to determine what actions, if any, should be taken.

There are several points in this analytical process at which errors can be introduced. Two of these are at and before the point of injection.

Sample mixtures may be derived from a number of sources, and may require a variety of preparations, including concentration, extraction and reaction. In order to maintain the integrity of the sample, these steps are kept to a minimum and, wherever possible, they are automated. It is also important that the skill level of those preparing the samples does not affect the integrity of the results.

Samples may also be dirty. That is, they may contain materials that remain in the injector, may not pass through the column at all, or may contaminate the detector. Such materials can cause the deterioration of the results of subsequent analyses.

To overcome some of these problems, injection liners are frequently used in the injector of the chromatography An injection liner is a narrow tube that fits inside the injector interior, literally providing a liner for the injector, and samples are injected into this liner tube rather than directly into the injector itself. Materials that would remain in the injector are thus deposited and remain in the liner instead, and when the liner becomes too contaminated with these materials it can be removed and replaced with a new liner.

Injection liners may also deliberately contain materials that selectively hold back compounds, by chemical or physical processes. These materials are called packing materials, and are able selectively to absorb specific components of the mixture.

In some instances the absorption of components in the liner packing material is reversible. That is, a material may be absorbed at a low temperature, and may thereafter be released by raising the temperature. One such packing material absorbs organic components at a low temperature, but allows water to pass freely through it at the same low temperature; the water can thus be diverted out of the system whilst the organic materials remain within the packing material. Subsequently, the gas flows within the system can be redirected, and the liner and its contents heated up so that the organic materials are then displaced into the column for analysis.

However, the liners themselves become contaminated, and need to be changed from time to time. This is frequently a difficult process, and one that is also very difficult to automate. It involves first cooling the injector, and then reducing the gas pressure in the chromatography system. When the pressure inside the injector is at atmospheric pressure, the top of the injector is opened. The top of the injector generally has a number of pipes attached to it. Getting the top off with the pipes attached is an operation requiring considerable operator skill and dexterity. Once the top is out of the way, the liner can be pulled out and removed. A new liner must then be placed in the injector, and the above process repeated in reverse before the next analysis can be started.

This replacement process involves significant skills and a number of steps at which leaks and other errors can be introduced. The process is also very difficult to automate. Even in an otherwise automatic system, the replacement of the liner tends to be a manual operation. This means, unfortunately, that very often the liner is left in place far longer than it should be, leading to deterioration of the performance of the injector, possible degradation of samples in the injector, and potential errors in the results presented to the analyst.

The present invention proposes a novel type of injection liner that can more easily be replaced either manually or automatically. More specifically, the invention suggests an injection liner the input end of which has a laterally-extending external flange against which in use there can be placed an injection septum for closing and sealing the input end, which septum is then sealed in place against the flange by a closure cap that fits tightly over and around the two. For use with an injector that itself directly supplies the carrier gas, the liner carries sealing means beyond the flange which can in use form a seal against the interior surface of the injector, so separating this region from the atmosphere and also from the injector's interior pressure.

In one aspect, therefore, the invention provides an injection liner for use in the injector of a gas chromatograph, the liner being in the form of an elongate tube having an input end and an output end, the input end bearing a laterally-extending external flange against which in use there can be sealed an injection septum closing the input end, a closure cap then fitting tightly over and around the septum and the flange so as to hold the septum in place.

The invention also provides the "use" combination of liner tube, septum and cap. Thus, it provides an injection liner in the form of an elongate tube having an input end and an output end, the input end bearing a laterally-extending external flange, and the liner including an injection septum, for fitting over the input end and sealing against the flange, and a closure cap for fitting tightly over and around the septum and the flange so as to hold the septum sealingly against the flange and close the input end.

The invention provides an injection liner for use in the injector of a gas chromatograph. The idea of gas chromatography, and of the injector used as part of the apparatus, and the utilisation of a liner for the injector, has been discussed hereinbefore, and needs no further comment at this time, save perhaps to note that the chromatograph may be one of those where the carrier gas flow has to be fed into the liner via a narrow tube passing through the septum or it may be one of those where the injector can be modified to supply the gas directly, and it passes into the liner through a special input aperture positioned between its ends and on the atmosphere side of the sealing means which seals the liner to the inside of the injector. This is discussed further hereinafter.

The invention's injection liner is in the form of an elongate tube having an input end and an output end. Although the dimensions of liners are chosen to fit the injectors with which they are to be utilised, a typical such liner is 80 mm (3.2 in) long with an internal diameter of 3 mm (⅛ in) and an external diameter of 5 mm (0.2 in), and is made of a borosilicate glass such as PYREX (Registered Trademark).

The liner's input end carries the flange against which the septum seals; the output end—or, rather, a short length of the tube leading to the output end—may conveniently be associated with a restriction either to improve the liner's ability to retain packing materials which may be placed therein, or to improve its ability to induce gas flows within it which encourage desired flow patterns, or both. Such a restriction can take many forms; for instance, the tube may be internally narrowed—profiled—to provide one or more, step or waisted portion, or the tube may be blocked with a porous plug.

The input end of the liner of the invention bears a laterally-extending flange—an outwardly-directed one—against which there can in use be sealed an injection septum closing the input end. The flange need not be very deep, provided it can support the septum pushed against it; a simple lip of three or four millimetre (an eighth of an inch or so) is usually sufficient. The flange is conveniently given a number of concentrically-circular ridges on its septum-facing surface so as in use to assist in maintaining a gas-tight seal between the septum and the flange.

In use, the liner's flanged output end has sealingly positioned against it an injection septum closing the input end. The purpose of this septum, a disc-like object matching the dimensions of the liner's flanged input end, is to close that input end while at the same time allowing a sample (of the material to be analysed) to be injected into the liner through the septum using a syringe-like object fitted with a fine needle that can be pushed through the septum and then withdrawn therefrom without leaving any significant hole. The septum must therefore be made of a rubbery material; a preferred such material is a suitable silicone rubber, and advantageously this is protected by a coating on each side in the form of a thin layer of poly-tetrafluoroethylene (PTFE).

In use, the septum closing the liner's input end is held in place with a closure cap fitting tightly over and around the septum and the flange. The cap can be screwed on (the exterior edge of the flange can constitute a suitable thread), it can be a shrink-fit over the septum and flange, or it can be crimped on (that is, be held tightly in place by distorting the material of the cap below the flange).

The cap may be made from, or enclose, magnetic material to assist in the manual or automatic removal and replacement of the liner, when required.

Conveniently, the cap extends in use laterally beyond the boundaries of the tube and flange, and can be used to provide a sealing surface against the input end of the injector.

Where—as noted hereinbefore—the liner is to be employed with a chromatograph which is one of those where the injector is able to supply the carrier gas directly, the liner includes a special gas input aperture positioned between its ends (and usually closely adjacent the input end), and between this aperture and the liner's output end there is sealing means which in use seals the liner to the inside of the injector. The sealing means is preferably an O-ring, suitably mounted around the exterior of the liner within a groove, or between wall-like ridges effectively defining such a groove, in/on the outside of the liner.

When in place in the injector, the liner may be held sealed in place by a downward force on the liner. This force would maintain the seal between the gas pressure inside the injector and the pressure of the surrounding ambient atmosphere.

In an application of the invention, individual samples may be stored in individual liners in an automatic or manual system for later analysis. The samples are placed in the liner, either directly or on to packing material as normal. The injection septum and cap are then fitted to the liner, and the complete assembly is stored in a storage container. When the sample is to be analysed, the liner, together with its septum and cap, are transferred to the injection port of the gas chromatograph, and sealed in place.

Injections are made into the liner and, when required, the liner is easily removed by reducing the gas pressure in the injector, removing the sealing force and simply withdrawing the liner manually or automatically, for example, with a magnet.

Various embodiments of the invention are now described, though by way of illustration only, with reference to the accompanying diagrammatic Drawings in which.

Figure 1:
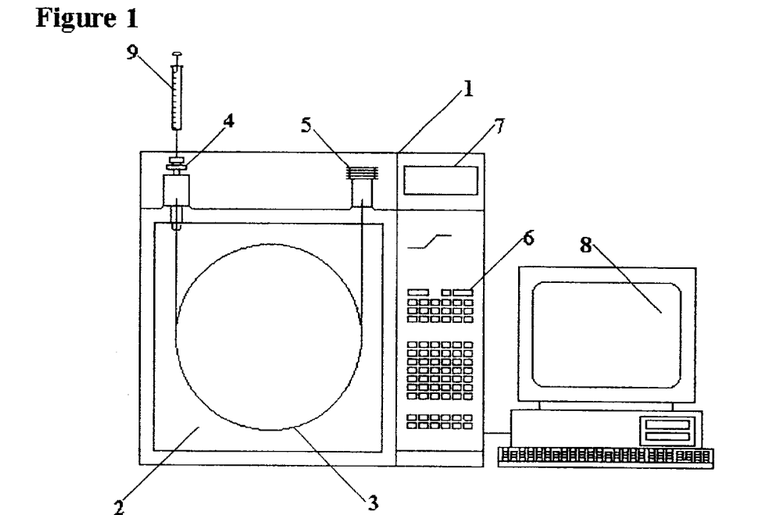
FIG. 1 shows a front view of a simple gas chromatograph system.

The gas chromatograph (1) shown in FIG. 1 consists of a column oven (2), in which the column (3) is mounted. At one end the column is connected to the injector (4), which is mounted in its own heated environment. At the other end the column is connected to the detector (5), which is also mounted in its own heated environment. The chromatograph is controlled via a keypad (6) and display (7). Signals from the detector 5 are amplified in the chromatograph and transferred to the data system (8), shown here as a computer.

Samples are injected into the injector 4 using the syringe (9), and are transported through the column 3 by carrier gas, separating in the normal chromatographic way. They emerge from the column 3 into the detector 5 as separated components.

Figure 2:
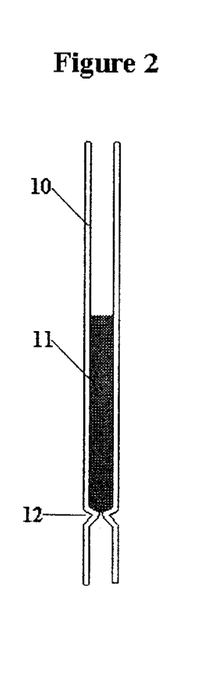
FIG. 2 shows a sectional view of a traditional injection liner.

A conventional liner is shown in FIG. 2. It consists of a glass, quartz or silica tube (10) filled with a packing material (11) and shaped (12) to improve the performance of the liner.

Figure 3:
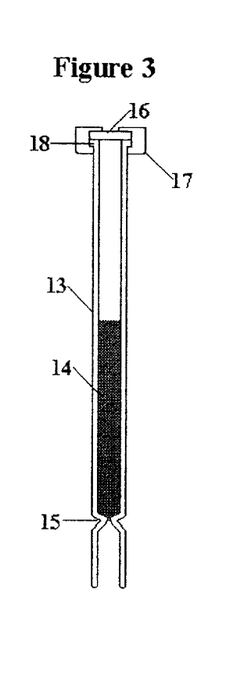
FIG. 3 shows a sectional view of an injection liner according to the invention and fitted with a septum and cap.

A liner of the invention is shown in FIG. 3. The new liner consists of a glass, quartz or silica tube (13). It also contains packing (14), and is shaped (15) to improve its performance. A shaped section (18) is built into the tube, forming an outwardly-projecting laterally-extending flange, so that the septum (16) can be housed on it and held gas tight in place by the septum cap (17).

Figure 4:
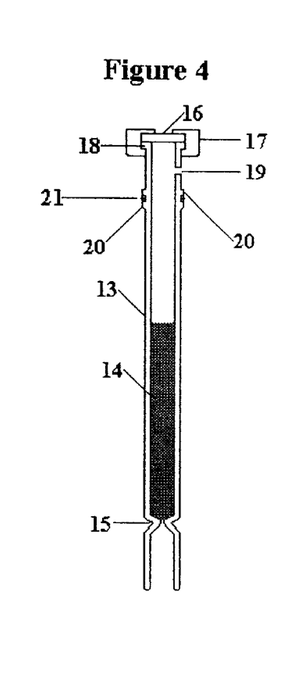
FIG. 4 shows a sectional view of another injection liner of the invention, this one having a gas inlet hole and seal.

A liner according to the invention and suitable for use where carrier gas can be supplied from within the injector is shown in FIG. 4. This embodiment of the new injection liner is provided with a gas inlet hole (19) and an O-ring seal 21 mounted within a locating channel defined by two walls (20).

Figure 5:
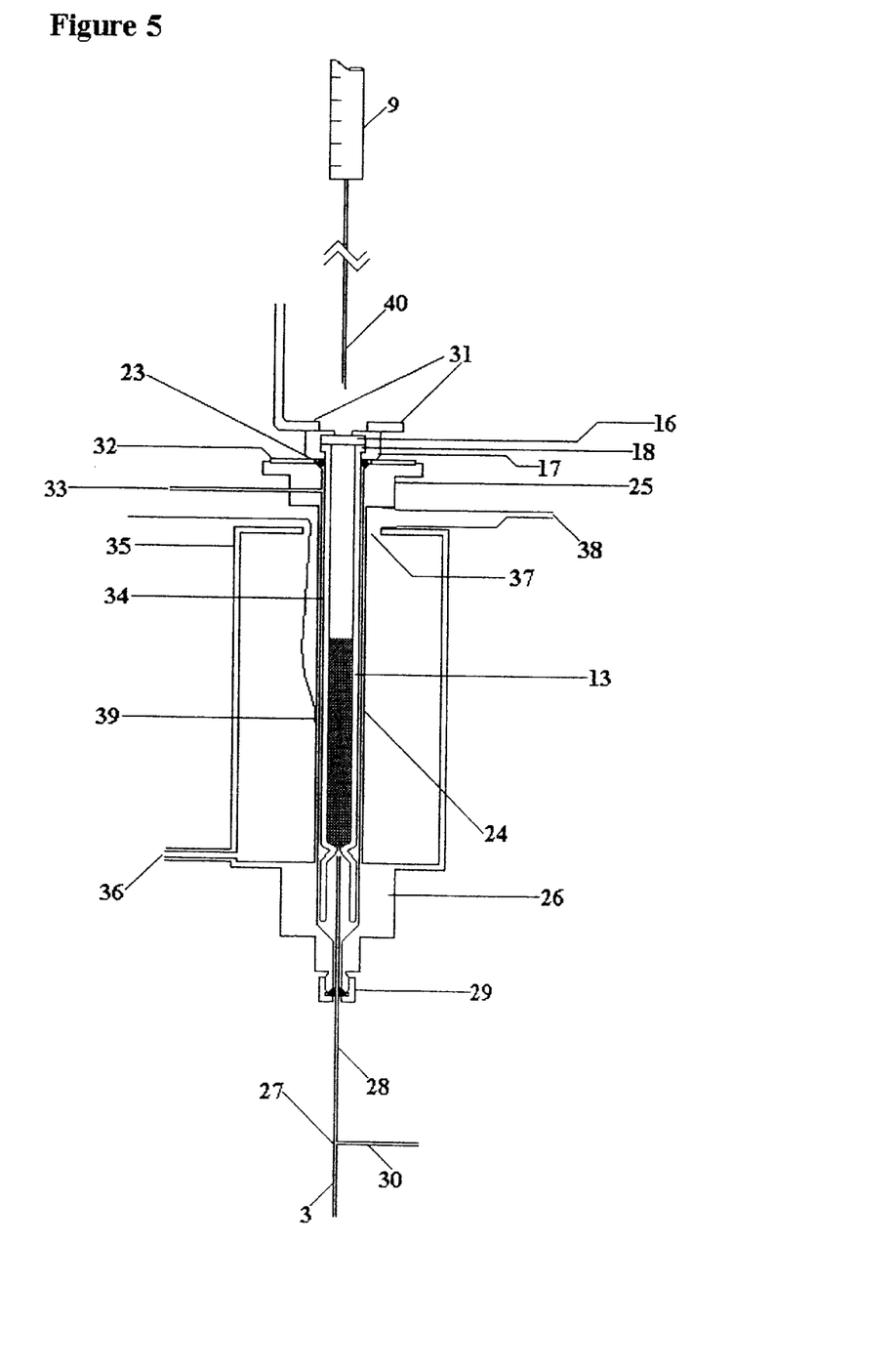
FIG. 5 shows a sectional view of a complete injector containing the injection liner of FIG. 3, where gas is to be supplied externally.
Figure 6:
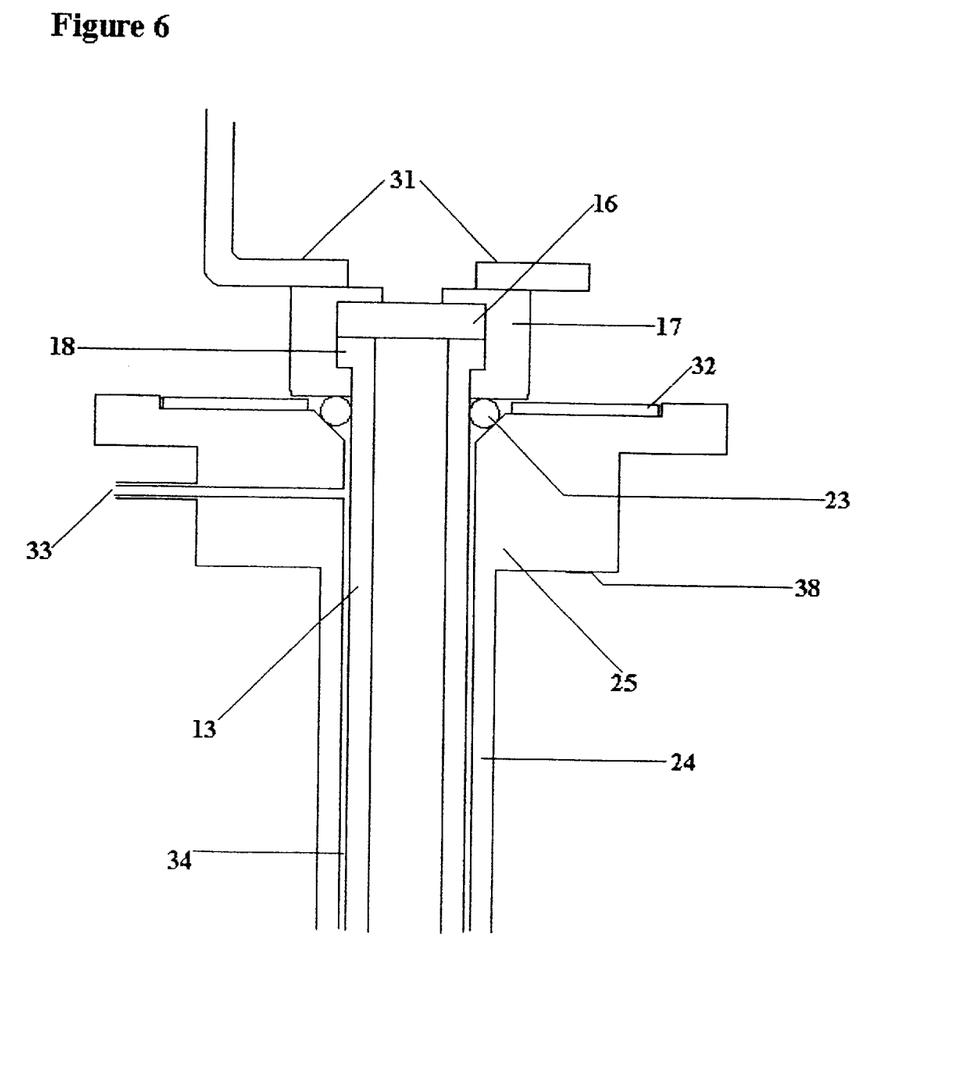
FIG. 6 shows detail at the top of the injector of FIG. 5.

FIGS. 5 and 6 show the use of a liner of the invention in a situation where carrier gas is to be supplied externally to the injector.

The complete injector consists of an outer tubular body (24) connected to a top (25) and a base (26). The column 3 is fitted into a tee piece (27) one arm of which is connected to the base of the injector 26 via a connecting tube (28), and sealed in place with a nut and ferrule (29), while the other arm of which is connected via a line (30) to a controllable gas supply (not shown).

The injection liner 13 fits within the tubular body 24 of the injector, and is held sealed in place at the top by a downward force from a pressure plate (31). This seals the tube 13 to the injector top 25 by the O-ring (23) because of the downward force transmitted through the septum cap 17. An insulating component (32) prevents contact between the septum cap 17 and the injector top 25, and also serves to ensure the optimal compression of the O-ring 23.

A split line (33) permits gas to flow out of the injector after it has passed up the annular space (34) between the liner 13 and the body 24, as required for normal split and split-less operation.

The remainder of the injector consists of an outer case (35), which permits cooling gas to be blown into the bottom of the injector (36) and out through the top (37). The injector can be heated by applying a voltage across the two electrical connections (38). This voltage resistively heats the body 24 of the injector, and hence the liner 13. Temperatures are controlled. using the signal from a temperature sensor (39).

The section (40) is shown separated from the rest of the syringe 9. In operation this section can either be part of the syringe or the end of a gas supply line.

Figure 7:
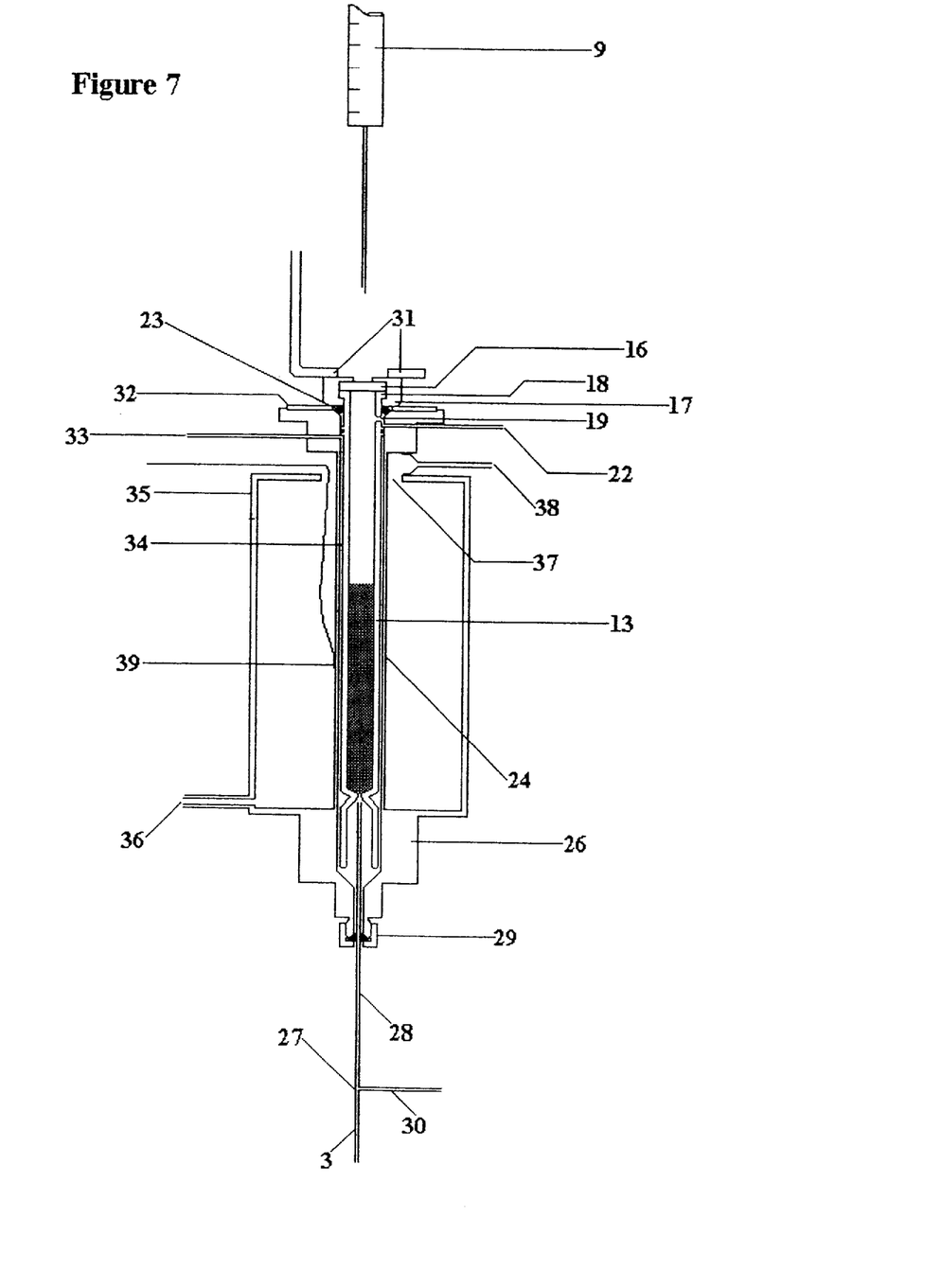
FIG. 7 shows a sectional view of a complete injector containing the injection liner of FIG. 4, where gas is to be supplied from within the injection system.
Figure 8:
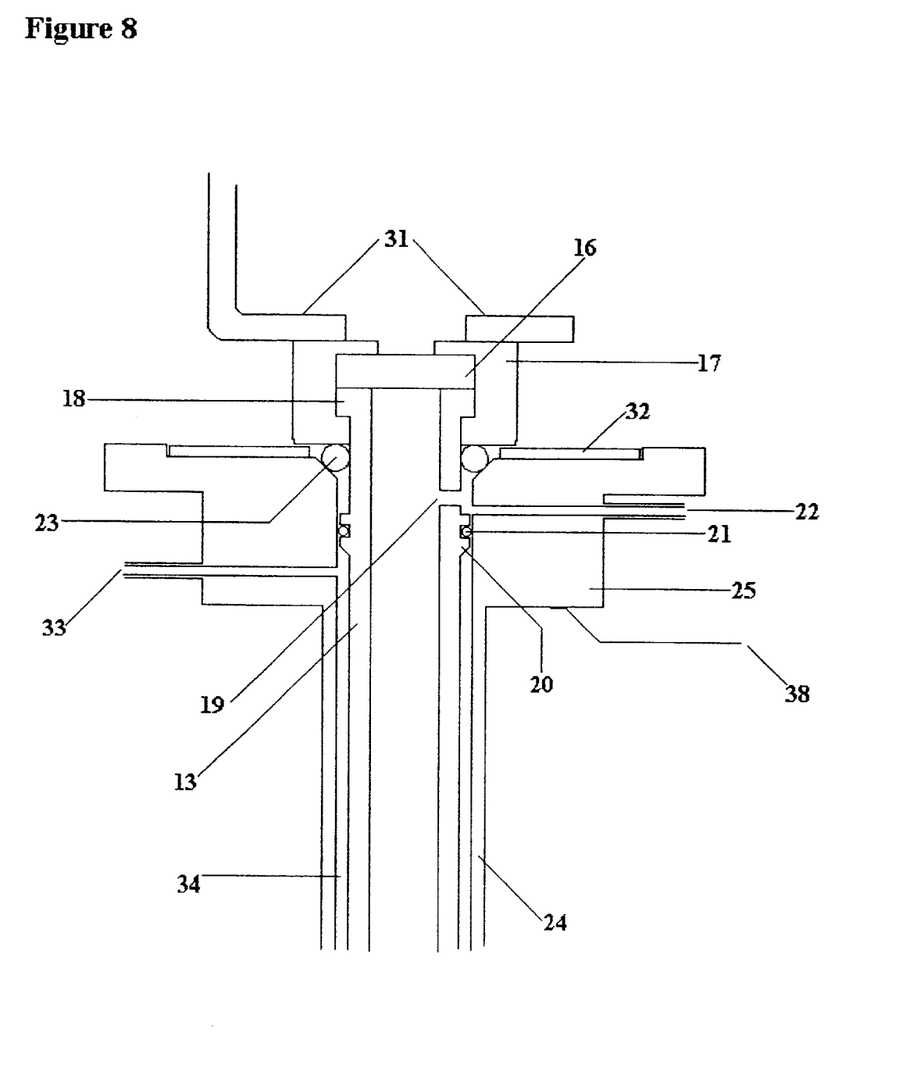
FIG. 8 shows detail at the top of the injector of FIG. 7.

An alternative embodiment is shown in FIGS. 7 and 8, where the injector is able to supply the carrier gas directly. In this case, the injection liner shown in FIG. 4 is used. This has the integral gas inlet hole 19, profiling 20 and seal 21. In this embodiment the injection liner 13 fits within the tubular body 24 of the injector, and is held sealed in place at the top by a downward force from a pressure plate 31. This seals the tube 13 to the injector top 25 by the O-ring 23 because of the downward force transmitted through the septum cap 17. An insulating component 32 prevents contact between the septum cap 17 and the injector top 25, and also serves to ensure the optimal compression of the O-ring 23.

A split line 33 permits gas to flow out of the injector after it has passed up the annular space 34 between the liner 13 and the body 24, as required for normal split and split-less operation.

The seal 21 is held in place by the local profiling 20 of the liner. Optimal compression for this seal is ensured by the design of the profiling. The seal serves to isolate the zone 34 of the injector, which is where the gas flows to the split line 33, from the top part of the injector, where gas can flow in through the inlet pipe 22, via the inlet hole 19 to the top of the liner. When required, gas is supplied through the inlet pipe 22, and is constrained to pass into the injection liner by the two O-rings 21 and 23. It passes into the top of the liner by way of the hole 19 and then on down the liner, as required The remainder of the injector consists of an outer case 35, which permits cooling gas to be blown into the bottom of the injector 36 and out through the top 37. The injector can be heated by applying a voltage across the two electrical connections 38. This voltage resistively heats the body 24 of the injector, and hence the liner 13. Temperatures are controlled using the signal from a temperature sensor 39.

Figure 9:
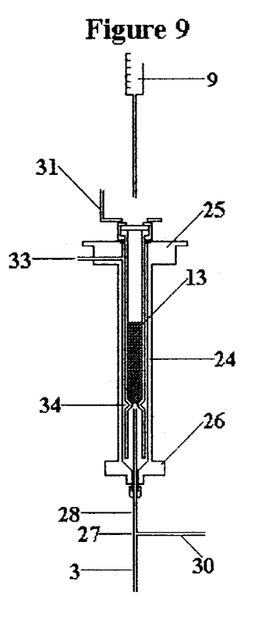
FIGS. 9,10,11 show a sequence relating to the use of an injection system like that of FIG. 5.

Operation of the system is now described with reference to the sequence of FIGS. 9–11. Before injection, the body 24 of the injector will generally have been cooled. Gas will flow in through the line 30 to the tee 27 supplying the column 3, and at the same time providing an upward gas flow into the injector via the line 28. From there, this upward flow passes up the annular space 34 between the liner 13 and the body 24 of the injector and out through the split line 33. The liner is held sealed in place by a downward force exerted by the pressure plate 31. A sample may be contained in the syringe 9, or may previously have been loaded in to the liner.

Figure 10:
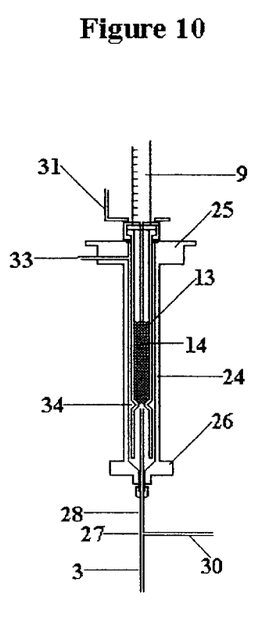

If—see FIG. 10—the sample has not been pre-loaded into the liner, then the syringe is moved down. It pierces the septum, and is pushed down until the tip of the needle reaches the correct position in the injection liner 13, generally just into the packing material 14. The plunger of the syringe is depressed at the appropriate rate, and the sample is ejected from the syringe. The syringe is then removed.

Figure 11:
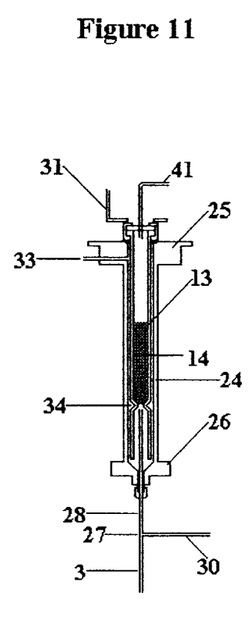

FIG. 11 shows the configuration where the injector is incapable of supplying the necessary gas. A gas supply pipe (41) is now inserted through the septum, and supplies the necessary carrier gas for the separation. The pressure plate 31 ensures that the liner remains in place. Gas now flows down through the liner 13 and the packing material 14. The temperature of the liner is raised to that required for the evaporation of the solvent by heating the body of the injector 24. During this phase gas continues to flow into the tee 27 from the line 30, which continues to supply the column 3 and to supply an upward flow through the line 28, thus preventing solvent from entering the column. Both gas flows, from the line 41 and the line 30 pass up the annular space 34 between the liner 13 and the injector body 24 and out through the split line 33. This ensures that the solvent is efficiently carried away after its removal from the sample matrix.

In the next phase the split line 33 is closed, and the pressures on the lines 30 and 41 are adjusted so that the flow through the line 30 passes downwards into the column 3 rather than upwards through the line 28. Gas from the line 41 at the top of the liner flows down through the liner, and then flows down through the line 28 and into the separation part of the system. A small flow may also be provided inwards through the split line 33 to prevent sample diffusion into the annular space 34 or the line 33. The body 24 of the injector is then heated to the temperature required to displace the sample from the liner, and the sample passes on to the column, possibly via a cryogenic focusing trap (not shown).

The configuration described for FIG. 11 is maintained during the separation process.

Figure 12:
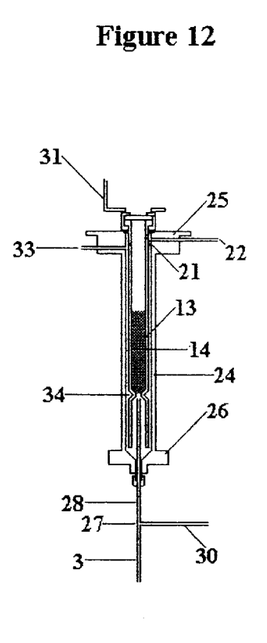
FIG. 12 shows the use of an injection system like that of FIG. 7.

In the case where the injector is capable of supplying the necessary carrier gas, the arrangement is as shown in FIG. 12. Gas passes into the injector via the gas supply pipe 22, and thence into the injection liner. The pressure plate 31 ensures that the liner remains in place. Gas now flows down through the liner 13 and the packing material 14. The temperature of the liner is raised to that required for the evaporation of the solvent by heating the body of the injector 24. During this phase, gas continues to flow into the tee 27 from the line 30, which continues to supply the column 3, and to supply an upward flow through the line 28, thus preventing solvent from entering the column. Both gas flows, from the line 22 and the line. 30, pass up the annular space 34 between the liner 13 and the injector body 24 and out through the split line 33. This ensures that the solvent is efficiently carried away after its removal from the sample matrix.

In the next phase the split line 33 is closed, and the pressures on the lines 22 and 30 are adjusted so that the flow through the, line 30 passes downwards into the column 3 rather than upwards through the line 28. Gas from the line 22 flows down through the liner, and then down through the line 28 and into the separation part of the system. A small flow may also be provided inwards through the split line 33 to prevent sample diffusion into the annular space 34 or the line 33. The body 24 of the injector is then heated to the temperature required to displace the sample from the liner, and the sample passes on to the column, possibly via a cryogenic focusing trap (not shown).

Figure 13:
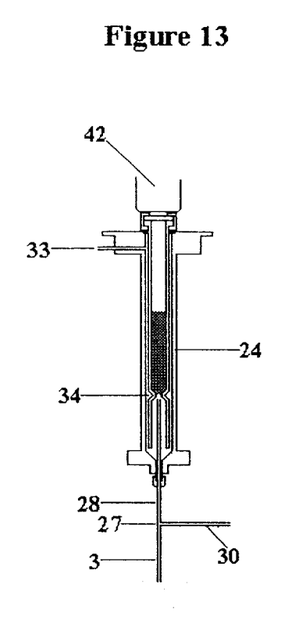
FIGS. 13,14 show a sequence relating to the removal of a liner of the invention.
Figure 14:
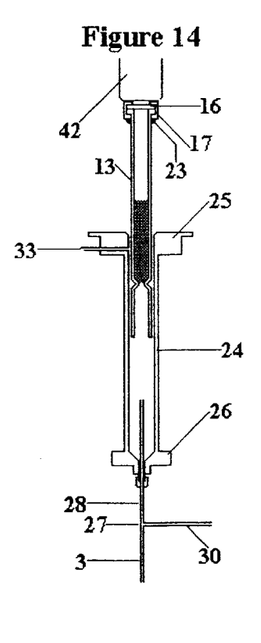

Whichever configuration is used, and referring to FIG. 13, at the end of the separation process the pressure balance in the system is altered such that the pressure at the top of the injector is reduced, and also gas is supplied upwards through the line 28 and down into the column 3 by the line 30. The gas line 41 is then removed if this configuration is being used. Gas continues to be supplied to the column, and up through the line 28 via the line 30. An extractor device (42) for removing the liner, such as an electromagnet, is applied to the top of the liner, and—as shown in FIG. 14—the liner 13 is removed, together with its 16, cap 17 and O-ring 23. The liner can then simply be replaced by insertion of a new liner, reversing the above removal process, followed by re-pressurisation.

This replacement operation can thus be performed with ease, either after every analysis or after a series of analyses have been carried out.

Figure 15:
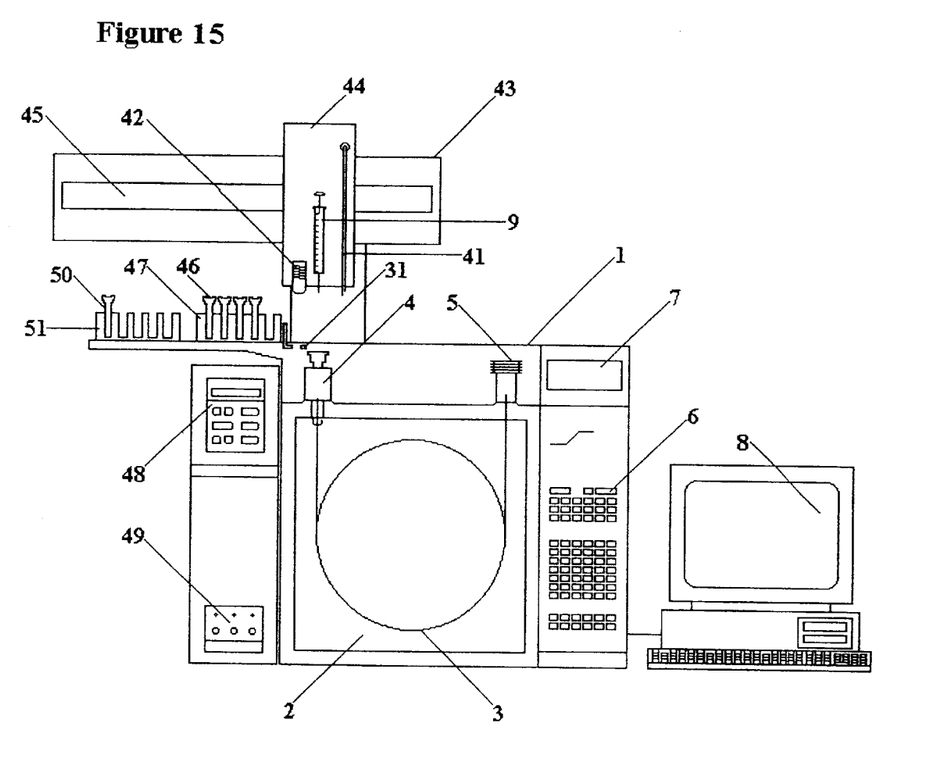
FIG. 15 shows a front view of an automatic gas chromatograph system using automatic storage and removal of the liner.

A fully automatic gas chromatography system, fitted with an automatic injector 43, is shown in FIG. 15. This injector controls the position of the injection mechanism (44) in all three axes, using motors and drives in tracks (45).

The injection mechanism 44 houses a conventional syringe 9, a gas supply pipe 41 (if required), and an electromagnet 42. Samples are stored in pre-loaded injection liners (46) in a storage rack (47) before analysis. When required, the sample is withdrawn from the rack 47 using the electromagnet 42 and placed in the injector 4. The pressure plate 31 holds the liner in place. The separation process is then carried out as described before under the control of the injector controller (48) and its associated gas and electrical controls (49), all under the supervision of the computer 8.

After analysis, gas flows are adjusted as previously described, and the pressure plate 31 is removed. The used liner is withdrawn by the electromagnet 42 and deposited (at 50) in the used liner rack (51).

The integral moulding—the flange at the input end of the liner—which provides the ability to fit the septum and septum cap, thus allows a very simple way of exchanging liners, both manually and automatically This enables the User to replace the liner whenever required, even as frequently as once per sample.

What is claimed is:

1. An injection liner for use in the injector of a gas chromatograph, the liner being in the form of an elongate tube having an input end and an output end, the input end bearing a laterally-extending external flange.

2. An injection liner as claimed in claim 1, wherein the liner's output end is associated with a restriction.

3. An injection liner as claimed in claim 2, wherein the flange has a number of concentrically-circular ridges on its septum-facing surface.

4. An injection liner as claimed in claim 3, wherein the liner includes a special gas input aperture positioned between its ends and between this aperture and the liner's output end there is exterior sealing means.

5. An injection liner as claimed in claim 4, wherein the sealing means is an O-ring, suitably mounted around the exterior of the liner between ridges on the outside of the liner.

6. An injection liner as claimed in claim 1, wherein the flange has a number of concentrically-circular ridges on a surfacing facing away from said tube.

7. An injection liner as claimed in claim 1, wherein the liner includes a special gas input aperture positioned between its ends and between this aperture and the liner's output end there is exterior sealing means.

8. An injection liner as claimed in claim 7, wherein the sealing means is an O-ring suitably mounted around the exterior of the liner between ridges on the outside of the liner.

9. An injection liner, as claimed in claim 1, in combination with
an injection septum, arranged to fit over the liner's input end and to fit sealingly against the liner's flange, and
a closure cap arranged to fit tightly over and around the septum and the flange so as to hold the septum sealingly against the flange and close the input end.

10. An injection liner as claimed in claim 9, wherein the input end has a thread thereon and the closure cap screws thereonto.

11. An injection liner combination as claimed in claim 10, wherein the septum is a disc-shaped object matching the dimensions of the liner's flanged input end and made of a silicone rubber protected by a coating on each side in the form of a layer of polytetrafluoroethylene (PTFE).

12. An injection liner combination as claimed in claim 10, wherein the closure cap is made from, or encloses, magnetic material.

13. An injection liner combination as claimed in claim 12, wherein the closure cap extends in use laterally beyond the boundaries of the tube and flange and provides a sealing surface.

14. An injection liner combination as claimed in claim 10, wherein the closure cap extends in use laterally beyond the boundaries of the tube and flange and provides a sealing surface.

15. An injection liner combination as claimed in claim 9, wherein the septum is a disc-shaped object matching the dimensions of the liner's flanged input end and made of a silicone rubber protected by a coating on each side in the form of a layer of polytetrafluoroethylene (PTFE).

16. An injection liner combination as claimed in claim 15, wherein the closure cap is made from, or encloses, magnetic material.

17. An injection liner combination as claimed in claim 16, wherein the closure cap extends in use laterally beyond the boundaries of the tube and flange and provides a sealing surface.

18. An injection liner combination as claimed in claim 15, wherein the closure cap extends in use laterally beyond the boundaries of the tube and flange and provides a sealing surface.

19. An injection liner combination as claimed in claim 9, wherein the closure cap is made from, or encloses, magnetic material.

20. An injection liner combination as claimed in claim 19, wherein the closure cap extends in use laterally beyond the boundaries of the tube and flange and provides a sealing surface.

21. An injection liner combination as claimed in claim 9, wherein the closure cap extends in use laterally beyond the boundaries of the tube and flange and provides a sealing surface.

* * * * *